United States Patent
Schmidt-Richberg et al.

(10) Patent No.: US 10,984,533 B2
(45) Date of Patent: Apr. 20, 2021

(54) METHOD AND APPARATUS FOR SEGMENTING A TWO-DIMENSIONAL IMAGE OF AN ANATOMICAL STRUCTURE

(71) Applicant: KONINKLIJKE PHILIPS N.V., Eindhoven (NL)

(72) Inventors: Alexander Schmidt-Richberg, Hamburg (DE); Irina Waechter-Stehle, Hamburg (DE); Martin Bergtholdt, Hamburg (DE); Jochen Peters, Norderstedt (DE); Rolf Jürgen Weese, Norderstedt (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 67 days.

(21) Appl. No.: 16/343,822

(22) PCT Filed: Oct. 20, 2017

(86) PCT No.: PCT/EP2017/076854
§ 371 (c)(1),
(2) Date: Apr. 22, 2019

(87) PCT Pub. No.: WO2018/077747
PCT Pub. Date: May 3, 2018

(65) Prior Publication Data
US 2019/0251692 A1     Aug. 15, 2019

(30) Foreign Application Priority Data
Oct. 25, 2016  (EP) .................................... 16195436

(51) Int. Cl.
*G06K 9/00*     (2006.01)
*G06T 7/11*     (2017.01)
(Continued)

(52) U.S. Cl.
CPC .............. *G06T 7/11* (2017.01); *G06T 7/0012* (2013.01); *G06T 7/12* (2017.01); *G06T 7/149* (2017.01);
(Continued)

(58) Field of Classification Search
CPC ........... G06T 19/20; G06T 2207/10072; G06T 2207/10132; G06T 2207/30048;
(Continued)

(56) References Cited

U.S. PATENT DOCUMENTS

| | | | |
|---|---|---|---|
| 6,106,466 A | 8/2000 | Sheehan et al. | |
| 7,386,153 B2 * | 6/2008 | Kim | G06T 7/11 382/128 |

(Continued)

FOREIGN PATENT DOCUMENTS

| | | |
|---|---|---|
| WO | 02093494 A2 | 11/2002 |
| WO | 2005078666 A1 | 8/2005 |

(Continued)

OTHER PUBLICATIONS

International Search Report and Written Opinion, International Application No. PCT/EP2017/076854, dated Dec. 7, 2017.
(Continued)

*Primary Examiner* — Jose L Couso

(57) ABSTRACT

A method and apparatus for segmenting a two-dimensional image of an anatomical structure includes acquiring (202) a three-dimensional model of the anatomical structure. The three-dimensional model includes a plurality of segments. The acquired three-dimensional model is adapted to align the acquired three-dimensional model with the two-dimensional image (204). The two-dimensional image is segmented by the plurality of segments of the adapted three-dimensional model.

20 Claims, 4 Drawing Sheets

(51) Int. Cl.
*G06T 7/12* (2017.01)
*G06T 7/149* (2017.01)
*G06T 7/00* (2017.01)
*G16H 30/40* (2018.01)

(52) U.S. Cl.
CPC ............... *G06T 2207/10072* (2013.01); *G06T 2207/10132* (2013.01); *G06T 2207/30048* (2013.01); *G16H 30/40* (2018.01)

(58) Field of Classification Search
CPC . G06T 2207/20116; G06T 2207/10081; G06T 2207/30101; G06T 2207/10124; G06T 2207/20016; G06T 2207/30004; G06T 2207/30016; G06T 2207/30064; G06T 2207/20128; G06T 2207/10136; G06T 2207/30081; G06T 2207/30028; G06T 2207/30096; G06T 2210/41; G06T 2200/04; G06T 2200/24; G06T 2219/004; G06T 2219/028; G06T 2219/2021; G06T 7/11; G06T 7/12; G06T 7/149; G06T 7/0012; G06T 7/143; G06T 7/174; G06T 7/10; G06T 7/73; G06T 7/74; G06T 17/00; G06T 17/20; G06T 17/205; G06T 15/08; G06T 15/205; G16H 30/40; G16H 30/20; G16H 50/50; G16H 50/20; A61B 8/0833; A61B 8/466; A61B 8/483; A61B 90/37; A61B 34/10; A61B 2034/105; G01S 15/8993; G01S 7/52068; G06F 19/321; G06F 19/00; G06K 9/38; G06K 9/6226; G06K 9/34; G06K 9/342; G06K 9/6207; Y10S 128/916

See application file for complete search history.

(56) References Cited

U.S. PATENT DOCUMENTS

| | | | | |
|---|---|---|---|---|
| 7,706,610 B2* | 4/2010 | Zhang | ................. | G06K 9/6226 |
| | | | | 382/173 |
| 9,965,863 B2* | 5/2018 | Xu | ................. | G06T 7/0012 |
| 2005/0004446 A1 | 1/2005 | Cowan | | |
| 2007/0014452 A1* | 1/2007 | Suresh | ................. | G06T 17/20 |
| | | | | 382/128 |
| 2011/0102549 A1* | 5/2011 | Takahashi | ............. | A61C 1/084 |
| | | | | 348/46 |
| 2016/0045317 A1* | 2/2016 | Lang | .................. | G05B 19/4099 |
| | | | | 700/98 |
| 2016/0228194 A1* | 8/2016 | Park | ........................ | G06T 19/20 |
| 2016/0232655 A1* | 8/2016 | Lachner | ................. | G06T 7/337 |
| 2017/0181809 A1* | 6/2017 | Panescu | ................ | A61B 8/466 |
| 2020/0323561 A1* | 10/2020 | Park | ........................ | G06T 7/13 |
| 2020/0364865 A1* | 11/2020 | Donhowe | ............. | A61B 34/30 |

FOREIGN PATENT DOCUMENTS

| | | |
|---|---|---|
| WO | 2011127940 A1 | 10/2011 |
| WO | 2016110463 A1 | 7/2016 |

OTHER PUBLICATIONS

Van Assen, H. et al., "Spasm: A 3D-ASM for segmentation of sparse and arbitrarily oriented cardiac MRI data", Medical Image Analysis, 2006, pp. 286-303.

Ma, M. et al., "Model driven quantification of left ventricular function from sparse single-beat 3D echocardiography", Medical Image Analysis, 2010, pp. 582-593.

Ma, M. et al., "Left ventricle segmentation from contrast enhanced fast rotating ultrasound images using three dimensional active shape models", FIMH, 2009, The Netherlands.

Van Assen, H. et al., "SPASM: Segmentation of sparse and arbitrarily oriented cardiac MRI data using a 3D-ASM", Spain, FIMH, 2005.

J. Weese, I. Wächter-Stehle, L. Zagorchev, J. Peters: Shape-Constrained Deformable Models and Applications in Medical Imaging. PR-TN technical Note 2013/00749, Philips Research Laboratories, Hamburg, Dec. 2012.

Wang, X. et al., "Adaptive Mesh Expansion Model (AMEM) for Liver Segmentation from CT Image", PLOS One, Mar. 2015.

* cited by examiner

METHOD AND APPARATUS FOR SEGMENTING A TWO-DIMENSIONAL IMAGE OF AN ANATOMICAL STRUCTURE

This application is the U.S. National Phase application under 35 U.S.C. § 371 of International Application No. PCT/EP2017/076854, filed on 20 Oct. 2017, which claims the benefit of European Application Serial No. 16195436.7, filed 25 Oct. 2016. These applications are hereby incorporated by reference herein.

FIELD OF THE INVENTION

The invention relates to the field of medical imaging and, in particular, to a method and apparatus for segmenting a two-dimensional image of an anatomical structure.

BACKGROUND OF THE INVENTION

Medical imaging is a useful tool for providing visual representations of anatomical structures (for example, organs) in images. There exist many different types of medical imaging techniques including computed tomography (CT), magnetic resonance (MR), ultrasound (US), and similar. The images acquired from medical imaging can prove valuable for clinical analysis of a subject and, where necessary, medical intervention.

In many clinical applications, the accurate segmentation of two-dimensional (2D) images as well as three-dimensional (3D) images is required. Three-dimensional, or volumetric, images usually cover the whole object of interest (which may, for example, be an anatomical structure or part of an anatomical structure). The segmentation of three-dimensional images can benefit from context information in all three spatial directions. Moreover, the topology of the object in a three-dimensional image is consistent. On the other hand, two-dimensional images are often superior in terms of signal-to-noise ratio and spatial and/or temporal resolution. However, while algorithms have been proposed for the segmentation of multiple slices with known spatial relations, these algorithms cannot be employed for a single two-dimensional image. Also, the algorithms do not benefit from models learned from three-dimensional data.

Some existing techniques for segmenting two-dimensional images involve learning two-dimensional shapes from slice images. However, these techniques are impacted by inconsistencies in the placement of the scan plane during image acquisition. Also, depending on the exact scan plane, the topology of the two-dimensional contours may change. Moreover, the amount of training data available from two-dimensional scans is limited since only model points that lie on the slice of the training image are affected for each training instance.

WO 2016/110463 discloses a method in which two-dimensional image data of an object is segmented by applying a two-dimensional model to the two-dimensional image data, where the two-dimensional model is determined from a three-dimensional model. However, in this approach, the derived model cannot compensate for variances or inaccuracies in the choice of scan plane for the two-dimensional image data. Moreover, the volumetric information is lost in the process of creating the two-dimensional model and thus can no longer be used for visualisation or computation of certain parameters (such as the volume of certain anatomical structures).

Therefore, the existing techniques for segmenting two-dimensional images are susceptible to inaccuracies and only limited information can be acquired from two-dimensional images segmented using the existing techniques.

There is thus a need for an improved method and apparatus for segmenting a two-dimensional image of an anatomical structure.

SUMMARY OF THE INVENTION

As noted above, the limitations with existing approaches for segmenting two-dimensional images are that the techniques used are susceptible to inaccuracies and only limited information can be acquired from two-dimensional images segmented using these techniques. It would thus be valuable to have a method and apparatus that can segment a two-dimensional image of an anatomical structure to overcome these existing problems.

Therefore, according to a first aspect of the invention, there is provided a method for segmenting a two-dimensional image of an anatomical structure. The method comprises acquiring a three-dimensional model of the anatomical structure, the three-dimensional model comprising a plurality of segments, and adapting the acquired three-dimensional model to align the acquired three-dimensional model with the two-dimensional image. The two-dimensional image is segmented by the plurality of segments of the adapted three-dimensional model.

In some embodiments, the acquired three-dimensional model may comprise a view plane associated with the two-dimensional image. In some embodiments, the view plane associated with the two-dimensional image may comprise a two-dimensional plane through the anatomical structure. In some embodiments, the two-dimensional plane through the anatomical structure may be defined with respect to one or more anatomical features associated with the anatomical structure. In some embodiments, the acquired three-dimensional model may be adapted to align with the two-dimensional image based on the view plane associated with the two-dimensional image. In some embodiments, the acquired three-dimensional model may be adapted to align with the two-dimensional image based on any one or more of a spatial position of the view plane and an orientation of the view plane.

In some embodiments, the acquired three-dimensional model may comprise information associated with one or more of the plurality of segments, the information corresponding to one or more characteristic features of the anatomical structure. In some embodiments, the acquired three-dimensional model may be adapted to align with the two-dimensional image based on the information corresponding to the one or more characteristic features of the anatomical structure.

In some embodiments, adapting the acquired three-dimensional model to align with the two-dimensional image may comprise any one or more of rotating the acquired three-dimensional model to align the acquired three-dimensional model with the two-dimensional image, and translating the acquired three-dimensional model to align the acquired three-dimensional model with the two-dimensional image. In some embodiments, adapting the acquired three-dimensional model to align with the two-dimensional image may comprise restricting the degrees of freedom of the acquired three-dimensional model.

In some embodiments, adapting the acquired three-dimensional model may comprise minimising an energy functional that attracts the three-dimensional model to the two-dimensional image to align the three-dimensional model with the two-dimensional image. In some embodiments, the energy functional may comprise any one or more of an internal energy term that constrains a shape of the three-dimensional model to an anatomically reasonable shape, an external energy term that deforms the three-dimensional model towards one or more characteristic feature points in the two-dimensional image, and a further energy term that restricts a deformation of the three-dimensional model to a view plane associated with the two-dimensional image.

In some embodiments, the method may further comprise processing the adapted three-dimensional model to determine a value for at least one parameter of the anatomical structure. In some embodiments, the at least one parameter may comprise any one or more of a volume of at least part of the anatomical structure and a thickness of at least part of the anatomical structure.

According to a second aspect of the invention, there is provided a computer program product comprising a computer readable medium, the computer readable medium having computer readable code embodied therein, the computer readable code being configured such that, on execution by a suitable computer or processor, the computer or processor is caused to perform the method or the methods described above.

According to a third aspect of the invention, there is provided an apparatus for segmenting a two-dimensional image of an anatomical structure. The apparatus comprises a processor configured to acquire a three-dimensional model of the anatomical structure, the three-dimensional model comprising a plurality of segments, and adapt the acquired three-dimensional model to align the acquired three-dimensional model with the two-dimensional image. The two-dimensional image is segmented by the plurality of segments of the adapted three-dimensional model.

In some embodiments, the processor may be configured to control one or more user interfaces to render the segmented two-dimensional image.

According to the aspects and embodiments described above, the limitations of existing techniques are addressed. In particular, the above-described aspects and embodiments allow for the segmentation of two-dimensional images using three-dimensional models. By using three-dimensional models to segment two-dimensional images, more information can be acquired about the anatomical structure in the two-dimensional image (for example, about the shape of the anatomical structure out of the plane). The segmented two-dimensional images acquired according to the above-described aspects and embodiments can be used for a better visualization of the anatomical structure. Furthermore, the aspects and embodiments can employ many well-tested three-dimensional models that are already available and these volumetric models are not susceptible to variances in the choice of scan plane. Also, employing available three-dimensional models allows the knowledge already gained from these models to be exploited and saves resources. Therefore, the aspects and embodiments described above enable a successful application of three-dimensional models for two-dimensional image segmentation.

There is thus provided an improved method and apparatus for segmenting a two-dimensional image of an anatomical structure, which overcomes the existing problems.

BRIEF DESCRIPTION OF THE DRAWINGS

For a better understanding of the invention, and to show more clearly how it may be carried into effect, reference will now be made, by way of example only, to the accompanying drawings, in which.

DETAILED DESCRIPTION OF THE EMBODIMENTS

As noted above, the invention provides an improved method and apparatus for segmenting a two-dimensional image of an anatomical structure, which overcomes the existing problems.

Figure 1:
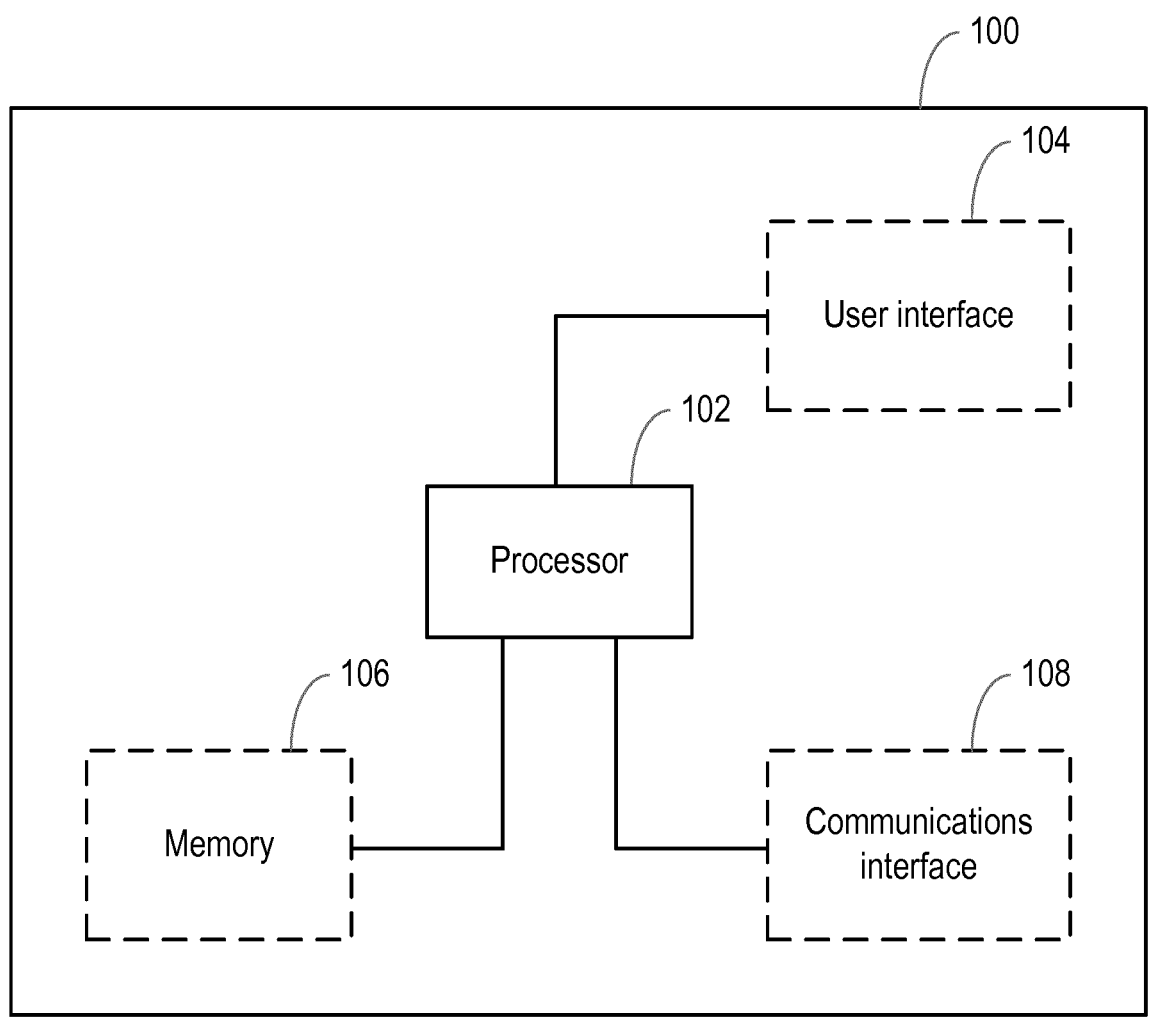
FIG. 1 is a block diagram of an apparatus according to an embodiment.

FIG. 1 shows a block diagram of an apparatus 100 according to an embodiment that can be used for segmenting a two-dimensional (2D) image of an anatomical structure. The two-dimensional image can be a two-dimensional medical image such as a two-dimensional computed tomography (CT) image, a two-dimensional magnetic resonance (MR) image, a two-dimensional ultrasound (US) image, a two-dimensional positron emission tomography (PET) image, a two-dimensional single photon emission computed tomography (SPECT) image, a two-dimensional nuclear medicine image, or any other two-dimensional medical image. The two-dimensional image may be a single slice (or a single plane).

The anatomical structure in the two-dimensional image may be an organ such as a heart, a lung, an intestine, a kidney, a liver, or any other anatomical structure. The anatomical structure in the two-dimensional image can comprise one or more anatomical parts. For example, a two dimensional image of the heart can comprise a ventricle, an atrium, an aorta, and/or any other part of the heart. Although examples have been provided for the type of two-dimensional image and for anatomical structure (and the parts of the anatomical structure) in the two-dimensional image, it will be understood that the invention may also be used for segmenting any other type of two-dimensional image and any other anatomical structures in the two-dimensional image.

The apparatus 100 comprises a processor 102 that controls the operation of the apparatus 100 and that can implement the method describe herein. The processor 102 can comprise one or more processors, processing units, multi-core processors or modules that are configured or programmed to control the apparatus 100 in the manner described herein. In particular implementations, the processor 102 can comprise a plurality of software and/or hardware modules that are each configured to perform, or are for performing, individual or multiple steps of the method according to embodiments of the invention.

Briefly, the processor 102 is configured to acquire a three-dimensional (3D) model of the anatomical structure in the two-dimensional (2D) image and adapt the acquired three-dimensional model to align the acquired three-dimensional model with the two-dimensional image. The three-dimensional model comprises a plurality of segments and the two-dimensional image is segmented by the plurality of segments of the adapted three-dimensional model.

In some embodiments, the apparatus 100 may also comprise at least one user interface 104. Alternatively or in addition, at least one user interface 104 may be external to (i.e. separate to or remote from) the apparatus 100. For example, at least one user interface 104 may be part of another device.

A user interface 104 may be for use in providing a user of the apparatus 100 (for example, a healthcare provider, a healthcare specialist, a care giver, a subject, or any other user) with information resulting from the method according to the invention. The processor 102 may be configured to control one or more user interfaces 104 to provide information resulting from the method according to the invention. For example, the processor 102 may be configured to control one or more user interfaces 104 to render the segmented two-dimensional image. Alternatively or in addition, a user interface 104 may be configured to receive a user input. In other words, a user interface 104 may allow a user of the apparatus 100 to manually enter instructions, data, or information. The processor 102 may be configured to acquire the user input from one or more user interfaces 104.

A user interface 104 may be any user interface that enables rendering (or output) of information, data or signals to a user of the apparatus 100. Alternatively or in addition, a user interface 104 may be any user interface that enables a user of the apparatus 100 to provide a user input, interact with and/or control the apparatus 100. For example, the user interface 104 may comprise one or more switches, one or more buttons, a keypad, a keyboard, a touch screen or an application (for example on a tablet or smartphone), a display screen, a graphical user interface (GUI) or other visual rendering component, one or more speakers, one or more microphones or any other audio component, one or more lights, a component for providing tactile feedback (e.g. a vibration function), or any other user interface, or combination of user interfaces.

In some embodiments, the apparatus 100 may also comprise a memory 106 configured to store program code that can be executed by the processor 102 to perform the method described herein. The memory 106 can also be used to store models, images, information, data, signals and measurements acquired or made by the processor 102 of the apparatus 100 or from any interfaces, memories or devices that are external to the apparatus 100. For example, the memory 106 may be used to store the two-dimensional image of the anatomical structure, one or more three-dimensional models of anatomical structures (which may, for example, comprise one or more three-dimensional models for the anatomical structure in the two-dimensional image), the adapted three-dimensional model, the segmented two-dimensional image, or similar.

In some embodiments, the apparatus 100 may also comprise a communications interface 108 for enabling the apparatus 100 to communicate with any interfaces, memories and devices that are internal or external to the apparatus 100. The communications interface 108 may communicate with any interfaces, memories and devices wirelessly or via a wired connection. For example, in an embodiment where one or more user interfaces 104 are external to the apparatus 100, the communications interface 108 may communicate with the one or more external user interfaces wirelessly or via a wired connection. Similarly, in an embodiment where one or more memories are external to the apparatus 100, the communications interface 108 may communicate with the one or more external memories wirelessly or via a wired connection.

It will be appreciated that FIG. 1 only shows the components required to illustrate this aspect of the invention, and in a practical implementation the apparatus 100 may comprise additional components to those shown. For example, the apparatus 100 may comprise a battery or other power supply for powering the apparatus 100 or means for connecting the apparatus 100 to a mains power supply.

Figure 2:
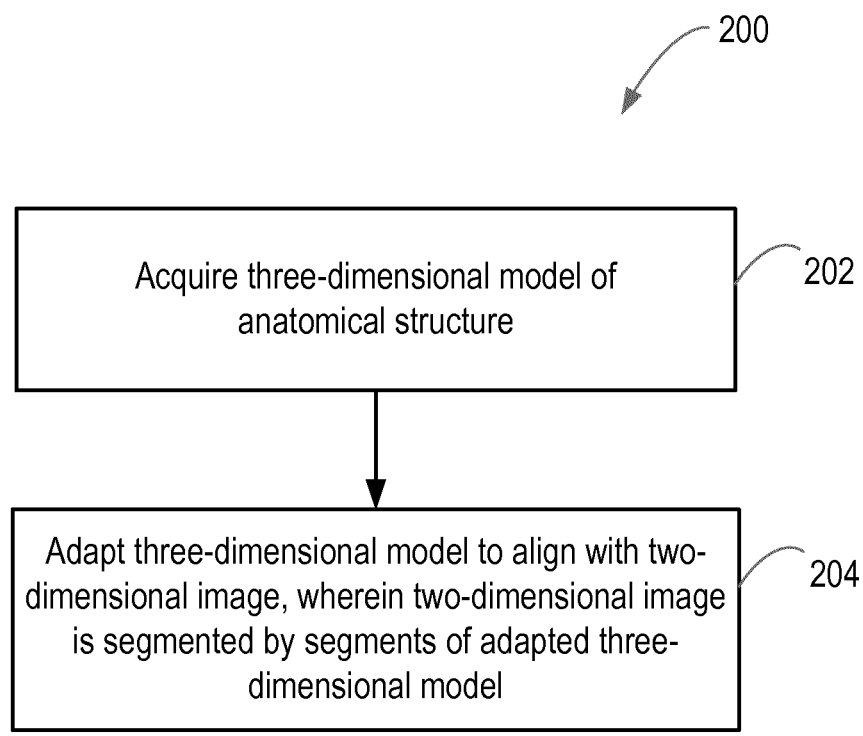
FIG. 2 is a flow chart illustrating a method according to an embodiment.

FIG. 2 illustrates a method 200 for segmenting a two-dimensional image of an anatomical structure according to an embodiment. The illustrated method 200 can generally be performed by or under the control of the processor 102 of the apparatus 100.

With reference to FIG. 2, at block 202, a three-dimensional model of the anatomical structure in the two-dimensional image is acquired. The three-dimensional model of the anatomical structure may comprise one or more anatomical parts that correspond to anatomical parts in the two-dimensional image of the anatomical structure. The three-dimensional model for the anatomical structure may be acquired from the memory 106 of the apparatus 100 or from a memory external to the apparatus 100. For example, the processor 102 of the apparatus may be configured to acquire the three-dimensional model for the anatomical structure from the memory 106 of the apparatus 100 or from a memory external to the apparatus 100. The three-dimensional model for the anatomical structure may be a deformable three-dimensional model. In some embodiments, the three-dimensional model for the anatomical structure can be a three-dimensional model that is trained based on volumetric image data associated with the anatomical structure (or three-dimensional images of the anatomical structure). For example, in some embodiments, the method may comprise a training phase in which three-dimensional models of one or more anatomical structures are learnt.

The three-dimensional model for the anatomical structure comprises a plurality of segments. For example, the three-dimensional model for the anatomical structure can comprise a mesh. Where the three-dimensional model of the anatomical structure comprises a plurality of anatomical parts, the three-dimensional model may comprise a sub-mesh corresponding to one or more of the plurality of anatomical parts. In some embodiments, the mesh (or sub-mesh) can be a triangular mesh. In other words, in some embodiments, the three-dimensional model for the anatomical structure may comprise a plurality of triangular segments. In embodiments in which the three-dimensional model comprises a sub-mesh corresponding to one or more of the plurality of anatomical parts, each sub-mesh may comprise a plurality of segments. Although examples are provided for the form of the segments in the three-dimensional model, it will be understood that the three-dimensional model for the anatomical structure may comprise any other shaped segments (or any other shaped mesh).

In some embodiments, the acquired three-dimensional model may comprise (for example, may define or identify) a view plane associated with the two-dimensional image. The view plane may comprise, for example, a two-dimensional plane through the anatomical structure. For example, the view plane may be a standardised two-dimensional plane through the anatomical structure (e.g. a two-dimensional plane through an anatomical structure that is defined with respect to one or more anatomical features or landmarks associated with the anatomical structure). Thus, a view plane can allow a standardised view of an anatomical structure. This facilitates, for example, better comparison between the anatomical structures of different subjects. View planes are defined in many anatomical imaging applications. For example, in fetal imaging, the abdominal circumference of the fetus is measured in the "abdominal circumference plane", which is defined as a plane orthogonal to the head-to-toe axis, running through the stomach and the upper part of the umbilical vein, whilst not passing through the heart. By defining such view planes, the variability in biometry measurements is minimized.

In embodiments where the acquired three-dimensional model comprises a view plane associated with the two-dimensional image, the acquired three-dimensional model may also comprise information corresponding to the view plane. For example, the model may comprise information defining the location of a view plane in the model (for example, the information may define the position of the view plane with respect to the model, e.g. the position of the view plane with respect to one or more mesh segments of the model). The view plane that is comprised in the three-dimensional model may enable rotation and/or translation of the three-dimensional model, such that the plane intersects the module (or, more specifically, the segments of the three-dimensional model). This allows for in-plane rotation and/or translation of the three-dimensional model. The information corresponding to the view plane may therefore be indicative of the location at which the view plane associated with the two-dimensional image intersects (or cuts) the acquired three-dimensional model (for example, if the two-dimensional image is taken on a particular view plane, information about the same view plane may be comprised in the model). For example, the acquired three-dimensional model may comprise information indicative of a spatial position of the view plane associated with the two-dimensional image in the three-dimensional model, an orientation of the view plane associated with the two-dimensional image in the three-dimensional model, or any other information, or any combination of information corresponding to the view plane. The information corresponding to the view plane associated with the two-dimensional image may be encoded in the three-dimensional model. In some embodiments, a label may be attached to each segment of the three-dimensional model that intersects the view plane associated with the two-dimensional image. In this way, it can be ensured that the view plane can be reconstructed by interpolating corresponding centre points of the segments (even after adaptation of the three-dimensional model). From the information corresponding to the view plane associated with the two-dimensional image, it is possible to establish a correspondence between the acquired three-dimensional model and the two-dimensional image to align the acquired three-dimensional model with the two-dimensional image, as will be described later.

Alternatively or in addition to the acquired three-dimensional model comprising information corresponding to a view plane, in some embodiments, the acquired three-dimensional model may comprise information associated with one or more of the plurality of segments. The information may, for example, correspond to one or more characteristic features of the anatomical structure. The one or more characteristic features of the anatomical structure may comprise characteristic features indicative of one or more boundaries in the anatomical structure. The boundaries may, for example, be indicative of different parts of the anatomical structure. Examples for the one or more characteristic features of the anatomical structure include, but are not limited to, an average shape of the anatomical structure, typical shape variations in the anatomical structure, appearance information for the anatomical structure, or any other characteristic feature, or combination of characteristic features of the anatomical structure. In embodiments in which the three-dimensional model for the anatomical structure comprises a mesh, the mesh can be representative of the characteristic features of the anatomical structure.

Returning back to FIG. 2, although not illustrated, the three-dimensional model is initially placed (or positioned) in the two-dimensional image. In some embodiments, the initial placement of the three-dimensional model in the two-dimensional image can comprise detecting the anatomical structure in the two-dimensional image to place the three-dimensional model at the location of the anatomical structure in the two-dimensional image. The anatomical structure may be detected in the two-dimensional image using any suitable feature extraction technique (such as the Generalized Hough Transformation, GHT, or any other feature extraction technique). For the initial placement of the three-dimensional model in the two-dimensional image, it may be assumed that the two-dimensional image shows a standardized view of the anatomical structure, such as a specific scan or image plane through the anatomical structure. For example, in an embodiment in which the two-dimensional image of the anatomical structure is a two-dimensional image of the heart, it may be assumed that the two-dimensional image shows a standardized view (e.g. a view plane) of the heart (such as a two chamber view, a three chamber view, a four chamber view, a short axis view, a long axis view, or any other standardized cardiac view).

Once the three-dimensional model is placed in the two-dimensional image, the three-dimensional model and the two-dimensional image are brought into correspondence. Thus, at block 204 of FIG. 2, the acquired three-dimensional model is adapted to align the acquired three-dimensional model with the two-dimensional image. For example, the acquired three-dimensional model may be iteratively adapted to align the acquired three-dimensional model with the two-dimensional image.

The adaptation of the acquired three-dimensional model to align with the two-dimensional image can comprise rotating the acquired three-dimensional model to align the acquired three-dimensional model with the two-dimensional image. For example, the acquired three-dimensional model may be rotated into the plane of the two-dimensional image. Alternatively or in addition, the adaptation of the acquired three-dimensional model to align with the two-dimensional image can comprise translating the acquired three-dimensional model to align the acquired three-dimensional model with the two-dimensional image. In this way, the three-dimensional model can be reoriented to match the orientation of the two-dimensional image. In some embodiments, adapting the acquired three-dimensional model to align with the two-dimensional image may comprise restricting the degrees of freedom of the acquired three-dimensional model.

In embodiments where the acquired three-dimensional model comprises a view plane associated with the two-dimensional image, the acquired three-dimensional model can be adapted to align with the two-dimensional image based on the view plane associated with the two-dimensional image. As mentioned earlier, it is possible to establish a correspondence between the acquired three-dimensional model and the two-dimensional image from the information corresponding to the view plane associated with the two-dimensional image to align the acquired three-dimensional model with the two-dimensional image. For example, the information corresponding to the view plane associated with the two-dimensional image can be used to establish a correspondence between a geometry of the acquired three-dimensional model and the two-dimensional image.

The correspondence between the acquired three-dimensional model and the two-dimensional image can be used to initialise adaptation of a position and/or orientation of the model (such as by rotation of the model, translation of the model, or similar) to align the acquired three-dimensional model with the two-dimensional image. The acquired three-dimensional model may be adapted to align with the two-dimensional image based on any one or more of a spatial position of the view plane, an orientation of the view plane, and any other feature associated with the view plane. In some embodiments, the adaptation of the three-dimensional model can reduce the degrees of freedom of the three-dimensional model to one or more planes (such as to in-plane, or mostly in-plane, motion and/or deformation). For example, the three-dimensional model may first be rotated into the view plane of the two-dimensional image according to information relating to an orientation of the view plane that is comprised (or encoded) in the three-dimensional model. Then, the three-dimensional model may be translated (for example, in-plane) to the correct position in the two-dimensional image using any suitable technique (such as a technique based on the Generalized Hough Transformation, GHT). An iterative affine and deformable adaption step may then follow to adapt the three-dimensional model to the contours in the two-dimensional image, which can be limited to in-plane motion.

In some embodiments, placement of the model in the image may alternatively or additionally be based on parameters relating to a coordinate system of the subject (for example, the orientation and/or the position of the subject with respect to the device used to create the two-dimensional image). For example, in cardiac imaging, a transducer may be placed close to the apex of the heart such that the atria are at the "far side" of the image (with respect to the direction of the travelling sound). Such positional information can be exploited for in-plane rotation and/or translation of the three-dimensional model in order to initially place the three-dimensional model as accurately as possible.

In embodiments where the acquired three-dimensional model comprises information corresponding to one or more characteristic features of the anatomical structure, the acquired three-dimensional model can be adapted to align with the two-dimensional image based on the information corresponding to the one or more characteristic features of the anatomical structure. In some embodiments, for example, adapting the acquired three-dimensional model based on the information corresponding to the one or more characteristic features of the anatomical structure can comprise adaptation (for example, an iterative adaptation) of the three-dimensional model into conformity with one or more characteristic features of the anatomical structure in the two-dimensional image. For example, one or more characteristic features of the acquired three-dimensional model may be matched (or mapped) to one or more corresponding characteristic features in the two-dimensional model and the one or more characteristic features of the acquired three-dimensional model may then be adapted into conformity with the one or more corresponding characteristic features of the anatomical structure in the two-dimensional image.

In some embodiments, one or more boundaries of the anatomical structure may be detected in the two-dimensional image. A boundary may, for example, be detected at a junction between different parts of the anatomical structure in the two-dimensional image. Then, for each segment of the acquired three-dimensional model, a target point (for example, a contour point) may be detected based on one or more characteristic features. This target point detection can comprise projecting a search ray into the plane of the two-dimensional image and detecting a target point along the projected search ray for each segment of the acquired three-dimensional model based on one or more characteristic features. This detection of target points along the projected search ray can prevent the technique from searching for target points that lie outside the image plane and thus areas that do not comprise image information. The one or more characteristic features may, for example, be automatically learned and can comprise, but are not limited to, grey values and/or edges. In these embodiments, the acquired three-dimensional model may be adapted through an attraction of a centre of one or more of the plurality of segments of the acquired three-dimensional model to the target point detected for that segment.

In some embodiments, adapting the acquired three-dimensional model may comprise minimising an energy functional E that attracts the three-dimensional model to the two-dimensional image to align the three-dimensional model with the two-dimensional image. The energy functional E may comprise an internal energy term $E_{int}$ that constrains a shape of the three-dimensional model to an anatomically reasonable shape. An anatomically reasonable shape is a shape that lies within a range of typical shape variations of the anatomical structure that is to be segmented and/or that differs within a predefined tolerance from a mean shape of the anatomical structure that is to be segmented. In other words, the internal energy term $E_{int}$ can ensure that the adapted three-dimensional model (or the final shape of the adapted three-dimensional model) is reasonable in terms of a known anatomy for the anatomical structure.

Alternatively or in addition, the energy functional E may comprise an external energy term $E_{ext}$ that deforms the three-dimensional model towards one or more characteristic feature points in the two-dimensional image. For example, in some embodiments, the external energy term $E_{ext}$ may be a term that deforms the three-dimensional model towards one or more planes (for example, target planes) orthogonal to one or more image gradients (for example, at the target points mentioned earlier) in the two-dimensional image. The external energy term $E_{ext}$ can stabilise the three-dimensional model such that it does not deviate (or does not deviate strongly or by more than a predefined amount) from the one or more planes.

In embodiments in which the energy functional E comprises an internal energy term $E_{int}$ and an external energy term $E_{ext}$, the energy functional may be determined as the sum of the internal energy term $E_{int}$ and an external energy term $E_{ext}$. For example, the energy functional E may be expressed as:

$$E := E_{int} + E_{ext}.$$

In embodiments in which the three-dimensional model comprises a mesh, the whole mesh may be adapted (or deformed) by minimising the energy functional comprising an internal energy term and external energy term.

Alternatively or in addition, the energy functional may comprise a further energy term that restricts (or constrains) a deformation (or adaptation) of the three-dimensional model to a view plane associated with the two-dimensional image. For example, the further energy term may restrict deformation of the three-dimensional model to in-plane motion or in-plane deformation. In some embodiments, the restriction (or constraint) on the adaptation of the three-dimensional model may comprise attaching one or more springs to one or more segments of the three-dimensional model. For example, one or more springs may be attached to one or more segments that intersect a view plane associated with the two-dimensional image. The addition of springs to one or more segments of the three-dimensional model can provide a more stable adaptation of the three-dimensional model.

Figure 3:
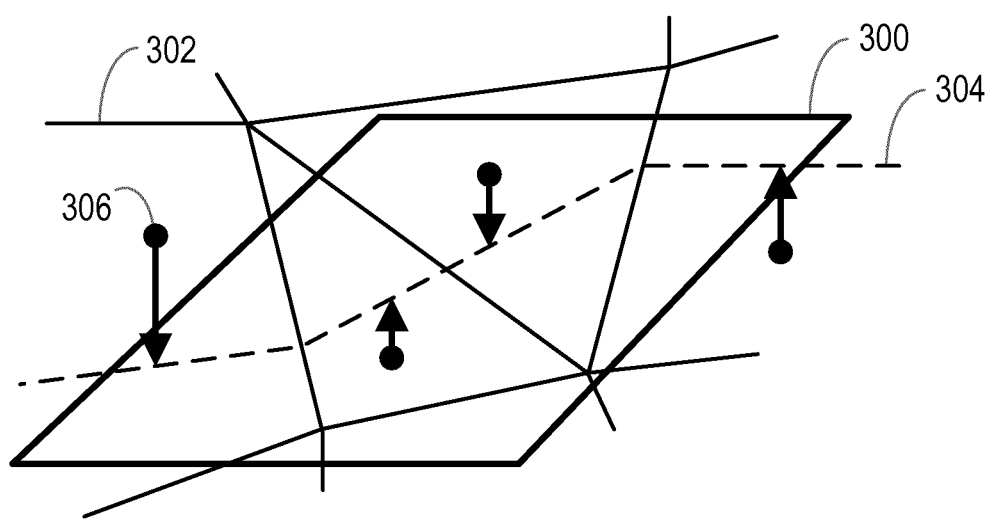
FIG. 3 is an illustration of a part of a three-dimensional model comprising a plurality of segments according to an embodiment.

FIG. 3 illustrates a part of a three-dimensional model of an anatomical structure comprising a plurality of segments 302 according to an example embodiment in which one or more springs 306 are attached to one or more of the plurality of segments. In this illustrated example embodiment, the three-dimensional model comprises a triangular mesh and thus the plurality of segments 302 comprise a plurality of triangular segments. However, as mentioned earlier, it will be understood that any other shaped segments (or any other shaped meshes) are also possible. As illustrated in this example embodiment, the springs 306 are attached to the segments 302 that intersect an image plane 300 of the two-dimensional image at an intersection line 304. The springs 306 are attached to the centre points of the intersecting segments 302 to restrict the motion of these segments with respect to the image plane 300. For example, the springs 306 can ensure that the intersecting segments 302 do not move more than a predefined distance from the image plane 300.

Thus, as described above, the energy functional may comprise any one or more of an internal energy term $E_{int}$, an external energy term $E_{ext}$, and a further energy term that restricts a deformation (or adaptation) of the three-dimensional model. In an example embodiment in which the energy functional E comprises an internal energy term $E_{int}$, an external energy term $E_{ext}$, and a further energy term that restricts a deformation (or adaptation) of the three-dimensional model, the energy functional may be determined as the sum of the internal energy term $E_{int}$, the external energy term $E_{ext}$, and the further energy term that restricts a deformation (or adaptation). In an example of such an embodiment, the energy functional E may be expressed as:

$$E:=E_{int}+E_{ext}+\Sigma_j w_j[(n_{plane})^T(c_j-x_j)]^2$$

Here, in the further energy term that restricts a deformation (or adaptation) of the three-dimensional model, $c_j$ denotes the centre points of the plurality of segments and $x_j$ denotes the corresponding target points in the image plane. In this embodiment, the distance between the target points is projected on the normal of the view plane (or the view plane vector), which is denoted by $n_{plane}$, to allow for in-plane motion and penalise (or discourage or prevent) out-of-plane motion. The transpose T of the view plane vector is used to determine the projection of $(c_j-x_j)$ on the normal $n_{plane}$ of the view plane. Optionally, the further energy term that restricts a deformation (or adaptation) can be weighted by a weighting factor $w_j$. The weighting factor $w_j$ can be adapted to allow the restriction (or constraint) to be relaxed or tightened. This can be useful where there is a high uncertainty in the choice of scan plane during acquisition of the two-dimensional image.

Finally, as the acquired three-dimensional model of the anatomical structure comprises a plurality of segments, the adapted three-dimensional model of the anatomical structure also comprises a plurality of segments. Thus, the two-dimensional image is segmented by the plurality of segments of the adapted three-dimensional model.

Thus, according to the method described herein, arbitrary two-dimensional images (or slices) of anatomical structures can be segmented. Moreover, this is possible without re-training features of the three-dimensional model provided that the features relevant to the two-dimensional image are encoded in the three-dimensional model. However, in some embodiments, the features (for example, one or more optimal features) of a three-dimensional model may be re-trained based one or more two-dimensional images. For example, this may allow a more specific adaptation of the three-dimensional model to the two-dimensional image of the anatomical structure, which may be particularly useful if the quality and/or resolution of the two-dimensional image varies considerably.

In any of the embodiments described herein, the method may further comprise rendering (or outputting or displaying) the segmented two-dimensional image to the user. In other words, the method may further comprise simultaneously rendering (or outputting or displaying) the adapted three-dimensional model comprising the plurality of segments and the two-dimensional image. In some embodiments, the processor 102 may control one or more user interfaces 104 (such as a display screen or a graphical user interface) to render (or output or display) the segmented two-dimensional image. In this way, a user can view the segmented two-dimensional image. This can be useful for medical analysis or assessment. Also, the simultaneous rendering of the adapted three-dimensional model comprising the plurality of segments and the two-dimensional image allows visualisation of the spatial relation between the adapted three-dimensional model and the two-dimensional image.

Figure 4B:
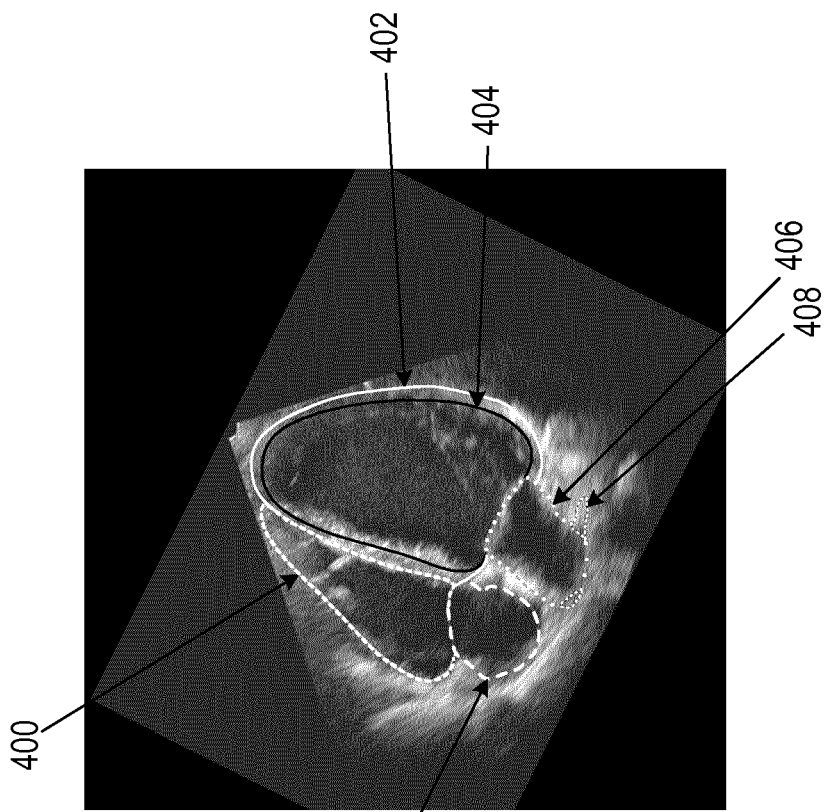
FIG. 4B is an illustration of a two-dimensional image according to an embodiment.
Figure 4A:
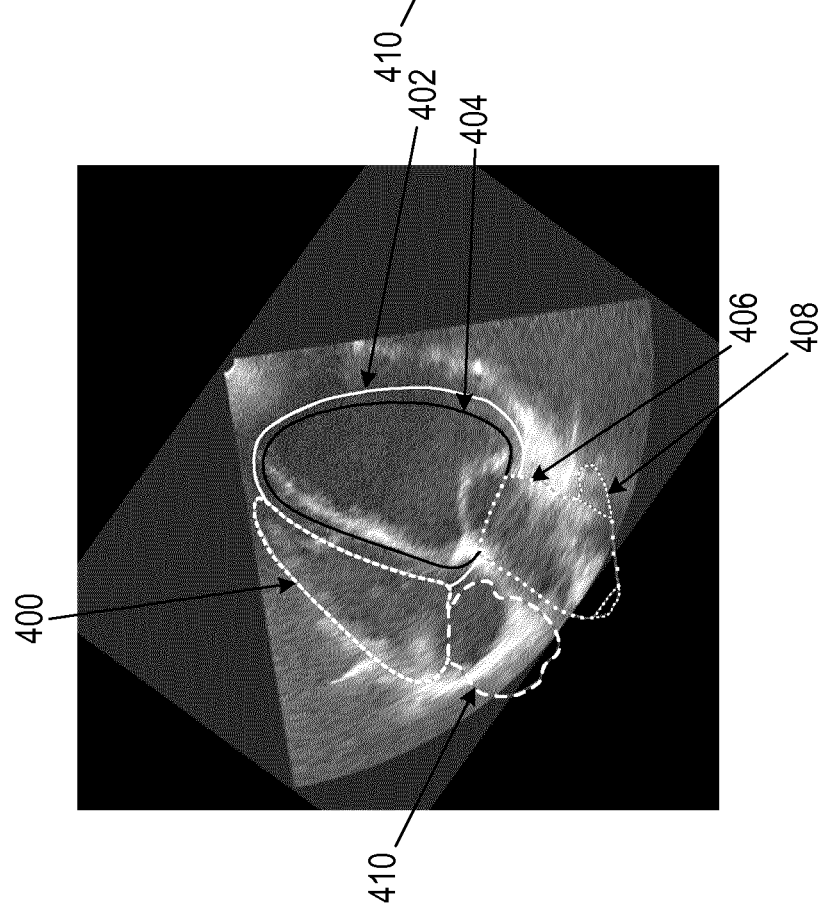
FIG. 4A is an illustration of a two-dimensional image according to an embodiment.

FIG. 4A is an illustration of a segmented two-dimensional image according to an embodiment prior to adaptation of the three-dimensional model to align with the two-dimensional image. In this example embodiment, a plurality of anatomical parts 400, 402, 404, 406, 408, 410 of an anatomical structure (which in this example is the heart) are defined by the three-dimensional model. For example, the plurality of anatomical parts comprise a ventricle, an atrium, an aorta and similar. After placement of the three-dimensional model in the two-dimensional image, the three-dimensional model comprising the plurality of segments is then adapted to align with the two-dimensional image.

FIG. 4B is an illustration of a segmented two-dimensional image according to an embodiment following adaptation of the three-dimensional model to align with the two-dimensional image. As illustrated in FIG. 4B, following the adaptation, the plurality of anatomical parts 400, 402, 404, 406, 408, 410 defined by the three-dimensional model are aligned to the corresponding parts of the anatomical structure in the two-dimensional image.

It will be understood that the method described herein is not restricted to a single two-dimensional image. In some embodiments, multiple two-dimensional images can be combined to achieve a segmentation that covers three-dimensional aspects. For example, a plurality of segmented two-dimensional images (such as two orthogonal two-dimensional images or any other plurality of segmented two-dimensional images) may be rendered (or output or displayed) simultaneously. In some such embodiments, cross-plane two-dimensional scans can define contours of the anatomical structure in two orthogonal slices and the adapted three-dimensional model can fit both contours and provide a model-based interpolation beyond the two-dimensional slices.

In any of the embodiments described herein, the method may further comprise processing the adapted three-dimensional model to determine a value for at least one parameter of the anatomical structure. The at least one parameter may be any parameter associated with the anatomical structure.

For example, the at least one parameter may comprise any one or more of a volume of at least part of the anatomical structure, a thickness of at least part of the anatomical structure, and any other parameter of the anatomical structure.

There is therefore provided an improved method and apparatus for segmenting a two-dimensional image of an anatomical structure. The method and apparatus described herein can be used for the segmentation of any arbitrary anatomical structures (for example, organs or any other anatomical structure) in two-dimensional images. The method and apparatus can be useful in medical imaging analysis and visualisation tools.

There is also provided a computer program product comprising a computer readable medium, the computer readable medium having computer readable code embodied therein, the computer readable code being configured such that, on execution by a suitable computer or processor, the computer or processor is caused to perform the method or methods described herein. Thus, it will be appreciated that the invention also applies to computer programs, particularly computer programs on or in a carrier, adapted to put the invention into practice. The program may be in the form of a source code, an object code, a code intermediate source and an object code such as in a partially compiled form, or in any other form suitable for use in the implementation of the method according to the invention.

It will also be appreciated that such a program may have many different architectural designs. For example, a program code implementing the functionality of the method or system according to the invention may be sub-divided into one or more sub-routines. Many different ways of distributing the functionality among these sub-routines will be apparent to the skilled person. The sub-routines may be stored together in one executable file to form a self-contained program. Such an executable file may comprise computer-executable instructions, for example, processor instructions and/or interpreter instructions (e.g. Java interpreter instructions). Alternatively, one or more or all of the sub-routines may be stored in at least one external library file and linked with a main program either statically or dynamically, e.g. at run-time. The main program contains at least one call to at least one of the sub-routines. The sub-routines may also comprise function calls to each other.

An embodiment relating to a computer program product comprises computer-executable instructions corresponding to each processing stage of at least one of the methods set forth herein. These instructions may be sub-divided into sub-routines and/or stored in one or more files that may be linked statically or dynamically. Another embodiment relating to a computer program product comprises computer-executable instructions corresponding to each means of at least one of the systems and/or products set forth herein. These instructions may be sub-divided into sub-routines and/or stored in one or more files that may be linked statically or dynamically.

The carrier of a computer program may be any entity or device capable of carrying the program. For example, the carrier may include a data storage, such as a ROM, for example, a CD ROM or a semiconductor ROM, or a magnetic recording medium, for example, a hard disk. Furthermore, the carrier may be a transmissible carrier such as an electric or optical signal, which may be conveyed via electric or optical cable or by radio or other means. When the program is embodied in such a signal, the carrier may be constituted by such a cable or other device or means. Alternatively, the carrier may be an integrated circuit in which the program is embedded, the integrated circuit being adapted to perform, or used in the performance of, the relevant method.

Variations to the disclosed embodiments can be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality. A single processor or other unit may fulfil the functions of several items recited in the claims. The mere fact that certain measures are recited in mutually different dependent claims does not indicate that a combination of these measures cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. A method for segmenting a two-dimensional image of an anatomical structure, the method comprising:
acquiring a three-dimensional model of the anatomical structure, the three-dimensional model comprising a plurality of segments and a view plane associated with the two-dimensional image; and
adapting the acquired three-dimensional model to align the acquired three-dimensional model with the two-dimensional image based on the view plane associated with the two-dimensional image; and
wherein the two-dimensional image is segmented by the plurality of segments of the adapted three-dimensional model, and
wherein adapting the acquired three-dimensional model to align with the two-dimensional image comprises restricting the degrees of freedom of the acquired three-dimensional model.

2. The method as claimed in claim 1, wherein the view plane associated with the two-dimensional image comprises a two-dimensional plane through the anatomical structure.

3. The method as claimed in claim 2, wherein the two-dimensional plane through the anatomical structure is defined with respect to one or more anatomical features associated with the anatomical structure.

4. The method as claimed in claim 1, wherein the acquired three-dimensional model is adapted to align with the two-dimensional image based on any one or more of a spatial position of the view plane and an orientation of the view plane.

5. An apparatus for segmenting a two-dimensional image of an anatomical structure comprising one or more computers or processors configured to perform the method as claimed in claim 1.

6. The method as claimed in claim 1,
wherein the acquired three-dimensional model comprises information associated with one or more of the plurality of segments, the information corresponding to one or more characteristic features of the anatomical structure, and
wherein the acquired three-dimensional model is adapted to align with the two-dimensional image based on the information corresponding to the one or more characteristic features of the anatomical structure.

7. The method as claimed in claim 1, wherein adapting the acquired three-dimensional model to align with the two-dimensional image comprises any one or more of:
rotating the acquired three-dimensional model to align the acquired three-dimensional model with the two-dimensional image; and
translating the acquired three-dimensional model to align the acquired three-dimensional model with the two-dimensional image.

8. The method as claimed in claim 1, wherein adapting the acquired three-dimensional model includes rotating the acquired three-dimensional model into the view plane of the two-dimensional image based on orientation information relating to the orientation of the view plane encoded in the three-dimensional model; and
wherein limiting the degrees of freedom includes limiting motion and deformation to in-plane motion and deformation in the viewing plane.

9. The method as claimed in claim 1, wherein adapting the acquired three-dimensional model includes minimizing an energy functional that attracts the three-dimensional model to the two-dimensional image to align the three-dimensional model with the two-dimensional image.

10. A method for segmenting a two-dimensional image of an anatomical structure, the method comprising:
acquiring a three-dimensional model of the anatomical structure, the three-dimensional model comprising a plurality of segments and a view plane associated with the two-dimensional image; and
adapting the acquired three-dimensional model to align the acquired three-dimensional model with the two-dimensional image based on the view plane associated with the two-dimensional image; and
wherein adapting the acquired three-dimensional model comprises minimizing an energy functional that attracts the three-dimensional model to the two-dimensional image to align the three-dimensional model with the two-dimensional image; and
wherein the energy functional comprises any one or more of:
an internal energy term that constrains a shape of the three-dimensional model to an anatomically reasonable shape;
an external energy term that deforms the three-dimensional model towards one or more characteristic feature points in the two-dimensional image; and
a further energy term that restricts a deformation of the three-dimensional model to a view plane associated with the two-dimensional image; and
wherein the two-dimensional image is segmented by the plurality of segments of the adapted three-dimensional model.

11. The method as claimed in claim 10, the method further comprising:
processing the adapted three-dimensional model to determine a value for at least one parameter of the anatomical structure.

12. The method as claimed in claim 11, wherein the at least one parameter comprises any one or more of a volume of at least part of the anatomical structure and a thickness of at least part of the anatomical structure.

13. A non-transitory computer program product comprising a computer readable medium, the computer readable medium having computer readable code embodied therein, the computer readable code being configured such that, on execution by a suitable computer or processor, the computer or processor is caused to perform the method as claimed in claim 1.

14. An apparatus for segmenting a two-dimensional image of an anatomical structure, the apparatus comprising:
a processor configured to:
segment a two-dimensional image of an anatomical structure,
acquire a three-dimensional model of the anatomical structure, the three-dimensional model including a plurality of segments and a view plane associated with the two-dimensional image,
adapt the acquired three-dimensional model to align the acquired three-dimensional model with the two-dimensional image based on the view plane associated with the two-dimensional image; and
wherein adapting the acquired three-dimensional model includes minimizing an energy functional that attracts the three-dimensional model to the two-dimensional image to align the three-dimensional model with the two-dimensional image;
wherein the energy functional includes any one or more of:
an internal energy term that constrains a shape of the three-dimensional model to an anatomically reasonable shape;
an external energy term that deforms the three-dimensional model towards one or more characteristic feature points in the two-dimensional image; and
a further energy term that restricts a deformation of the three-dimensional model to a view plane associated with the two-dimensional image,
wherein the two-dimensional image is segmented by the plurality of segments of the adapted three-dimensional model.

15. The apparatus as claimed in claim 14, wherein the processor is configured to control one or more user interfaces to render the segmented two-dimensional image.

16. The method as claimed in claim 10, further including:
rendering the segmented two-dimensional image on a user interface.

17. A non-transitory computer-readable medium carrying computer readable code configured such that, on execution by a suitable computer or processor, the computer or processor is caused to perform the method as claimed in claim 10.

18. The method as claimed in claim 10, wherein adapting the acquired three-dimensional model to align with the two-dimensional image comprises restricting the degrees of freedom of the acquired three-dimensional model.

19. An apparatus for segmenting a two-dimensional image of an anatomical structure comprising one or more computers or processors configured to perform the method as claimed in claim 10.

20. The apparatus as claimed in claim 19, further including:
a user interface;
wherein the one or more computers or processors are further configured to control the user interface to display the segmented two-dimensional image.

* * * * *